United States Patent [19]
Kennedy

[11] 3,987,545
[45] Oct. 26, 1976

[54] METHOD AND APPARATUS FOR MAKING A DENTAL PROSTHESIS IN SITU

[75] Inventor: Leland T. Kennedy, Richmond, Va.

[73] Assignee: IPCO Hospital Supply Corporation (Whaledent International Division), New York, N.Y.

[22] Filed: June 2, 1975

[21] Appl. No.: 582,813

[52] U.S. Cl. ................................................. 32/2
[51] Int. Cl.² ...................................... A61C 13/00
[58] Field of Search ....................................... 32/2

[56] References Cited
UNITED STATES PATENTS

| | | | |
|---|---|---|---|
| 3,421,222 | 1/1969 | Newman | 32/15 |
| 3,808,687 | 5/1974 | Millet | 32/2 |

Primary Examiner—Robert Peshock
Attorney, Agent, or Firm—Friedman, Goodman & Teitelbaum

[57] ABSTRACT

A method and apparatus are disclosed for forming a dental prosthesis in situ in a patient's mouth for the restoration of one or more missing, worn or broken teeth. The method includes forming a positive model of the patient's mouth and correcting the model by filling in the areas where restoration is required to correspond with the desired size and shape of the restored teeth, forming an elastomeric mold half of the areas to be restored using the model as a pattern, preparing the patient's teeth to receive the prosthesis by cutting down selected teeth, applying the elastomeric mold over the area of the patient's teeth and jaw where restoration is required so that a mold cavity is formed between the inner mold surface and the patient's jaw, pumping a vacuum in the mold cavity to test the seal of the elastomeric mold half relative to the jaw, releasing the vacuum if the seal holds, preparing a self-curing liquid resin molding material in a receptacle which is open to the atmosphere, connecting the mold cavity with the liquid resin in the receptacle through a flexible tube, closing the tube, drawing a vacuum in the mold cavity, opening the tube whereupon atmospheric pressure acting on the surface of the liquid in the receptacle forces the liquid resin into said mold cavity through the flexible tube, allowing the liquid resin to cure, and removing the mold from the patient's mouth.

The apparatus includes the elastomeric mold half prepared according to the above described method, a hand operated vacuum pump, a flexible exhaust tube connected between the vacuum pump and the elastomeric mold half, a flexible inlet tube connected between the elastomeric mold half and an open receptacle for containing a mix of cold curing liquid resin, and a clamp for closing and opening said inlet tube.

8 Claims, 12 Drawing Figures

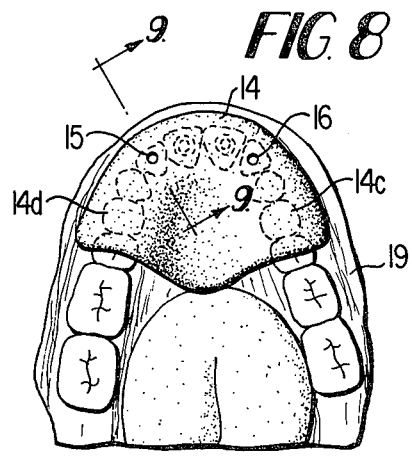
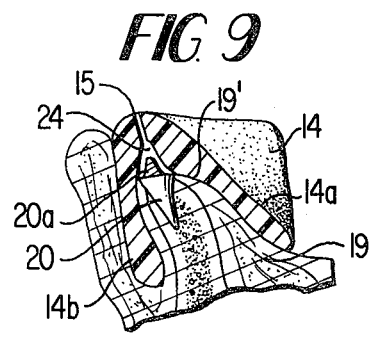
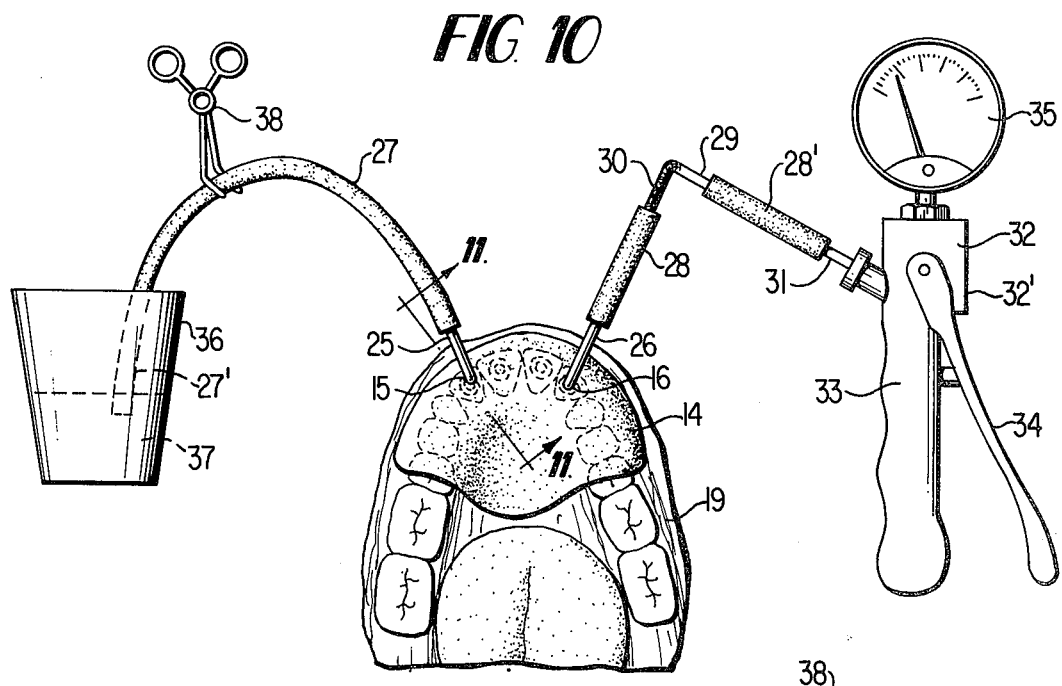
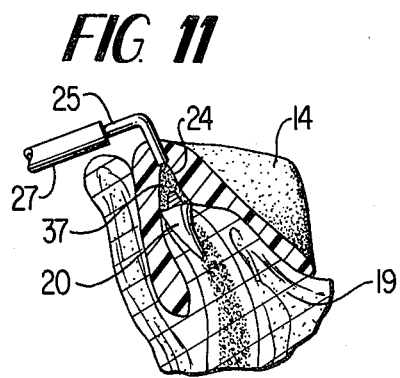
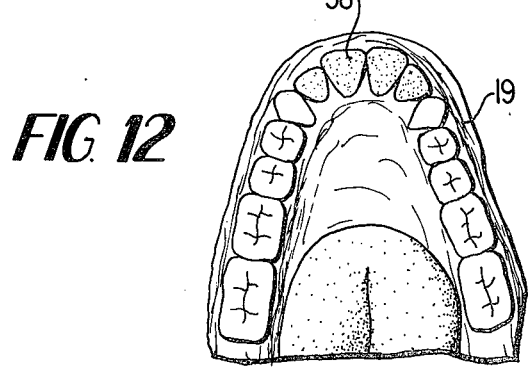

METHOD AND APPARATUS FOR MAKING A DENTAL PROSTHESIS IN SITU

BACKGROUND OF THE INVENTION

1. Field of the Invention:

The invention relates to an improved method and apparatus for molding a dental prosthesis in situ in a patient's mouth.

2. Description of the Prior Art:

It is broadly old to form a temporary prosthesis according to method steps outlined below:

1. Make a negative impression of the patient's mouth prior to the preparation of the teeth to receive a prosthesis;
2. Prepare the teeth to receive the prosthesis by cutting down as necessary, blocking out the undercuts on the prepared teeth and lubricating the prepared teeth to prevent the prosthesis forming material from sticking to the teeth;
3. Mix a cold curing acrylic resin mixture into a dough-like consistency;
4. Pack the dough-like mix of acrylic resin into the negative impression in the area to be restored;
5. Reseat the negative impression with the mass of acrylic resin in the mouth over the prepared teeth, the objective being to form a temporary prosthesis, the inner surface of which is formed by the surfaces of the cut down teeth and the outer surface of which is formed by the inner surface of the negative impression;
6. Allow the acrylic resin to cure;
7. Remove the impression from the mouth leaving the cured acrylic over the teeth; and
8. Remove the cured acrylic from the mouth and trim off any excess to form a temporary restoration to be worn by the patient while a permanent restoration is being made.

The method described above is beset by a number of disadvantages which the present invention seeks to overcome. When the dough-like mass of acrylic if formed by seating the impression holding the acrylic in place in the mouth, the dough-like mass of acrylic, which is in excess of the amount required to form the prosthesis, squeezes out between the impression and the mouth forming a flash around the restoration. This flash flows over the adjacent teeth and tissue creating a large mass of material which has to be trimmed from the restoration before it is usable. The flash formed does not permit the impression to be fully seated in the mouth resulting in the restoration (i.e. prosthesis) being oversized. Further recontouring of the restoration to bring the restoration into proper occlusal relationship with the opposing teeth in the other arch is thus required.

The doughiness of the acrylic mass exerts hydraulic pressure against the contour of the flexible impression material, thus deforming the surface of the prosthesis. The resulting deformaties must also be corrected.

During the removal of the prosthesis with the attached flash from the mouth, the prosthesis is warped to a certain degree. Also, during the trimming involved in removing the flash and recontouring the prosthesis to its proper shape, the prothesis is further distorted by handling and by the heat generated by the grinding of the acrylic resin. These deformities result in a prosthesis which does not fit back on the tooth stumps in an ideal manner and the poor fit of the prosthesis over the tooth stumps can lead to one or more of the following conditions:

1. Breakage of the prosthesis under mouth stresses created by the poor seating of the prothesis on the tooth stumps;
2. The rocking loose and coming out of the prothesis when subjected to mouth stresses.
3. Orthodontic movement of the teeth during mouth stress, resulting in a movable abutment tooth, in which case, a permanent bridge, when completed, would not seat properly and it would be necessary to remake the permanent bridge.

SUMMARY OF THE INVENTION

It is an object of the invention to provide an improved method and apparatus for making a dental prosthesis in situ without accompanying flash.

The method of the invention includes the formation of an elastomeric mold half over a positive model of the patient's jaw in the area where tooth restoration is required, preparation of the patient's teeth to receive the restoration by cutting down selected teeth, placing the elastomeric mold half over the area of the jaw where the tooth restoration is required, charging the mold with a cold setting, self curing liquid resin by a vacuum charging technique, allowing the resin to cure, and removing the elastomeric mold half from the patient's mouth leaving the molded prosthesis in place.

The apparatus of the invention includes the elastomeric mold which is formed over a positive model of a patient's jaw that has been corrected to the desired contour of the teeth which are to be restored, a pair of tubular fittings mounted in holes drilled through the mold into the mold cavity, a flexible exhaust tube connected to one of the fittings, a flexible inlet tube connected to the other fitting, a hand vacuum pump connected to the free end of the exhaust tube, a porous filter within the exhaust tube between the vacuum pump and the exhaust fitting, a releasable clamp for clamping and unclamping the inlet tube and an open receptacle for containing liquid cold-curing resin into which the free end of the inlet tube is inserted.

The formation of a dental prosthesis in situ according to the present invention includes the following advantages:

1. The mold is seated in place in the mouth before the material which is to be molded is introduced into the mold;
2. The cold curing resin mixture can be mixed to a thinner consistency than in the case where a doughy resin mixture is applied to a negative impression prior to being introduced into the mouth. (This is because the mold, according to the present invention, will be closed and sealed prior to introduction of the liquid resin into the mold. Flash, which is formed when the doughy mass held by the negative impression is forced out between the impression and the mouth, is avoided in the process of this invention);
3. The pressure used to force the liquid resin material into the mold, and the pressure holding the mold in place in the mouth are the same (i.e. barometric pressure);
4. When the mold is filled with the liquid resin the charging pressure is reduced to zero because the pressure inside and outside the mold is equalized.

The method of the present invention is especially adapted for molding temporary bridges for the restoration of missing, worn or broken teeth while a permanent bridge is being prepared by conventional processes. In preparing the teeth to receive the temporary bridge (i.e. prosthesis) two anchor teeth on opposite sides of the missing, worn or broken tooth (or teeth as the case may be) are cut down in size to serve as anchors for the prosthesis, an the worn or broken tooth (if present) is cut down to remove rough edges in the usual manner. The mold cavity according to the present invention includes the space between the elastomeric mold which has been formed over a corrected positive model and the cut down teeth and gum in the area of restoration.

BRIEF DESCRIPTION OF THE DRAWINGS

With the foregoing objects and features in view and such other objects and features which may become apparent as the specification proceeds, the invention will be understood from the following description taken in conjunction with the accompanying drawings, wherein like characters of reference designate like parts and wherein:

FIG. 8 is a plan view of the patient's jaw with the mold in place over the area to be restored;

FIG. 9 is a cross sectional view taken on line 9—9 of FIG. 8 and showing the mold cavity formed between the patient's jaw and the prepared mold;

FIG. 10 is a view similar to FIG. 8 but with the mold charging apparatus connected in place;

FIG. 11 is a cross sectional view taken on line 11—11 of FIG. 10 after liquid resin has been charged into the mold cavity;

FIG. 12 is a plan view of the patient's jaw showing the four restored front teeth.

DESCRIPTION OF THE PREFERRED EMBODIMENT

The invention will be described with reference to the drawings which illustrate the sequence of steps and apparatus for forming a dental prosthesis in situ.

In accordance with the method of the invention, a positive model 10 is made of the patient's jaw on which tooth restoration is required. This is done in a conventional manner by first taking a negative impression of the jaw, then pouring a mix of hard setting dental model forming material, such as dental stone, into the impression and allowing the mix to set, whereupon the impression is separated from the dental stone thus providing a positive model of the patient's existing dentition. The model is then corrected by adding wax to areas which are to be restored. Such areas include areas where there are missing teeth, broken parts of teeth, etc. The wax is shaped to the size and shape of the desired restoration and thus a model of the patient's jaw with the deficiencies of dentition corrected is obtained. For purpose of illustration, the areas of the model 10 which have been corrected include the front teeth 11 and 12 of the patient's lower jaw. The front teeth may have been knocked out, or broken as a result of an accident. In any case the dentist has determined that a permanent bridge is required to restore the missing or broken teeth, and while the permanent bridge is being prepared, a temporary bridge will be molded in situ according to the method of the invention.

After correcting the model, a mix of a room temperature vulcanizing silicone rubber (hereafter referred to as RTV silicone rubber) of a type which is commonly used in dentistry is prepared. The mix is applied to the corrected model to form a negative impression of the area which is to be restored, or bridged. It is necessary for the RTV silicone rubber mix to be spread over the area to be restored sufficiently thick so that upon setting, the silicon rubber may be handled without tearing. It is also necessary that the mix be spread to overlap the boundaries of the bridge area both mesio distally and gingivally in order to form a sealing boundary around the area of the bridge by about 10 MM or more. After the RTV silicone rubber mix is applied as described, the model 10 (with mix applied) is placed in a pressure pot. The pot is then closed and 30 pounds per square inch of air pressure is applied while the mix of RTV silicone rubber is curing. This provides for a denser cured silicone rubber and a better adaptation of the silicone rubber to the prepared model 10 than could be obtained by letting the RTV silicone rubber cure under normal room atmospheric conditions.

Figure 1:
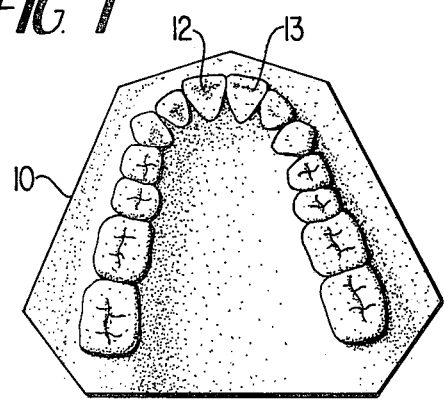
FIG. 1 is a top plan view of a corrected positive model made of a patient's jaw.
Figure 2:
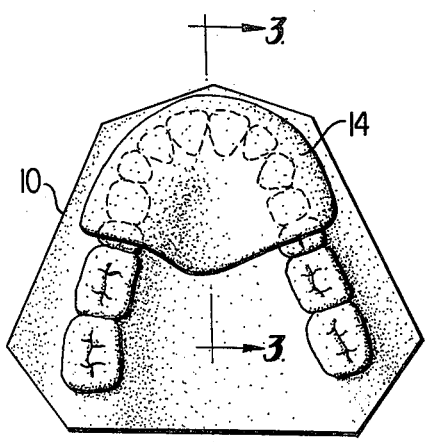
FIG. 2 is a top plan view of the model being used as a pattern with pliable mold forming material applied over the area of the jaw requiring tooth restoration to make an elastomeric mold of the patient's jaw.
Figure 3:
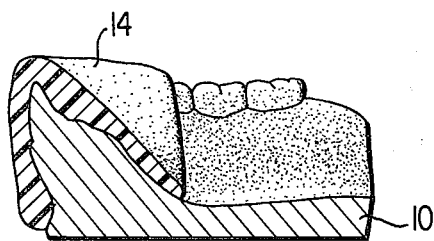
FIG. 3 is a cross sectional view taken on line 3—3 of FIG. 2.
Figure 4:
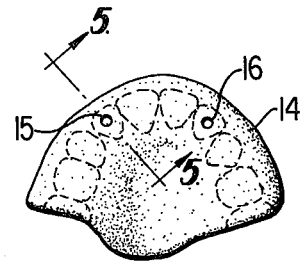
FIG. 4 is a top plan view of the elastomeric mold removed from the model with a pair of holes drilled through the mold at opposite ends of the area requiring tooth restoration.
Figure 5:
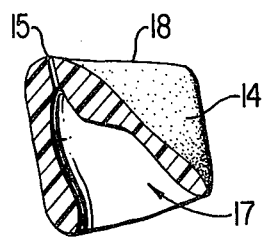
FIG. 5 is a cross sectional view taken on line 5—5 of FIG. 4.

Once the RTV silicone rubber mold 14 is cured, it is removed from the model 10, and it appears as shown in FIGS. 4 and 5. Thus, what is obtained is a negative impression of the area of the temporary bridge area (i.e. the restoration area) including a border which overlaps the restoration area by 10 millimeters or more. The negative impression formed of RTV silicone is an elastomeric mold half which fits in the patient's mouth over the area of the patient's jaw corresponding to the area of the model 10 over which the mold half 14 is made. The border area of the mold which overlaps the area designated for restoration provides a flexible gasket to seat around the area to receive the restoration. A pair of holes 15 and 16 are drilled through the elastomeric mold half from the inside of the groove 17 to the top side of the ridge 18 using a bur. The holes 15 and 16 are located at the mesial and distal occlusal surfaces of the imprint in the mold of the area of restoration obtained from the model 10.

Figure 6:
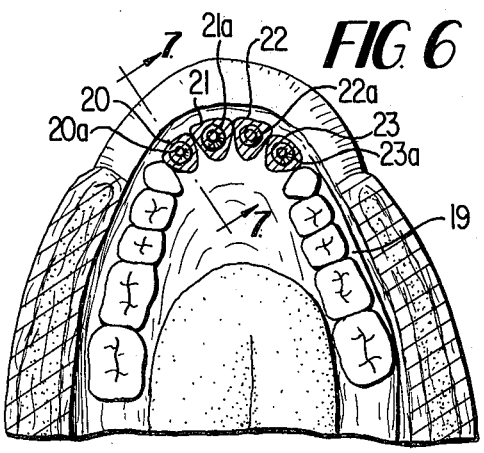
FIG. 6 is a plan view of the patient's jaw corresponding to the model illustrating four of the front teeth after they have been prepared for receiving the prosthesis.
Figure 7:
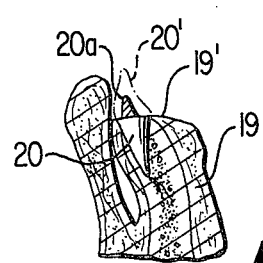
FIG. 7 is a cross sectional view taken on line 7—7 of FIG. 6 through one of the prepared teeth showing the outline of the original tooth in phantom and comparing it with the prepared tooth which has been cut down by grinding.

FIG. 6 shows the lower jaw 19 of a patient's mouth which has been prepared in a conventional manner to receive a bridge for the patient's front teeth 20, 21, 22, and 23. The teeth 21 and 22 are the teeth requiring a restoration and the teeth 20 and 23 are anchor teeth which have been cut down and will serve as anchors for the bridge. Each of the teeth in the restoration area have been cut down by grinding to provide stumps 20a, 21a, 22a, and 23a over which a temporary bridge will be molded in accordance with this invention and to which will be applied a permanent bridge after it has been prepared in a laboratory in the usual manner. Looking at FIG. 7, the original outline of the anchor tooth 20 which has been cut down to form the stump 20a is shown by the phantom line 20'.

After the patient's teeth have have been prepared in a manner as usually required for a permanent restoration, the elastomeric mold 14 is applied over the restoration area as shown in FIGS. 8–11. The mold cavity 24 as indicated in FIG. 9 comprises the space between the ridge 19' of the jaw 19 and the inside surfaces of the mold 14 which extend outwardly from the ridge 19'. The mold area 14a and 14b which are contiguous to the gum and the mold areas 14c and 14d covering the teeth outside the restoration area provide flexible gaskets which seal the mold cavity 24 relative to the patient's jaw 19.

Looking now at FIG. 10, the mold 14 is shown in position over the restoration area of the patient's jaw 19, with apparatus for charging the mold with a temporary bridge forming material connected to the mold. Two L-shaped tubular fittings 25 and 26 are placed in the holes 15 and 16 respectively from the outside of the mold 14, one leg of each tubular fitting being placed in the respective holes. To the other leg of each of the fittings 25 and 26 are connected flexible inlet and exhaust tubes 27 and 28 respectively of sufficient length to reach out of the patient's mouth. The exhaust tube 28 is connected by means of a third fitting 29 (containing a filter 30) to a second flexible exhaust tube 28' which inturn is connected to an inlet fitting 31 of a hand operated vacuum pump 32. The vacuum pump 32 is provided with a handle 33, and an operating lever 34 which is operatively connected to a reciprocating pistion (not shown) inside of the pump cylinder housing 32'. A vacuum gauge 35 is mounted on the cylinder housing 32' and is operatively connected to the inlet side of the pump 32. The assembly comprising the fitting 26, flexible tube 28, fitting 29, filter 30, flexible tube 28', fitting 31, the vacuum pump 32, and gauge 35 will be designated the mold exhaust assembly.

The free end 27' of the inlet tube 27 is adapted to be inserted into an open receptacle 36 in which a supply of liquid resin forming material 37 is placed. A clamp 38, which may be a hemostat, or other suitable hose clamp is provided for clamping the inlet hose. Instead of the hemostat, a person's fingers may be used as the clamp to close the inlet tube 27. The inlet tube 27 and inlet fitting 25 together with the exhaust assembly previously described comprise the mold charging means.

With the mold 14 and mold charging assembly provided as shown in FIG. 10, but without the liquid mix 37, a test is made of the apparatus by clamping the inlet tube 27 with the hemostat 38 to close the inlet and then operating the pump 32 until there is a vacuum of 27 or more inches of mercury. The pumping is then stopped and the vacuum should hold until released for a period of 15 seconds or more. When the vacuum holds, it is an indication that the mold fits properly and that the mold, fittings and various connections are sealed sufficiently to proceed with the actual molding of the restoration.

A mix 37 of tooth shaded, self curing liquid acrylic resin of a type commonly used in dentistry is then mixed in the receptacle 36. The free end 27' of the inlet tube 27 is then clamped with the hemostat 38 about one inch from the free end and the free end 27 is inserted into the mix of liquid resin 37. The vacuum pump 32 is then actuated until a vacuum of 27 inches or above of mercury is reached, whereupon the pumping is discontinued and the vacuum is held. The hemostat is then released from the tube 27 allowing it to open, whereupon the atmospheric pressure acting on the liquid resin 37 in the open receptacle 36 pushes the liquid resin through the inlet tube 27 into the mold cavity 24. Care is taken that the end 27' of the inlet tube 27 remains submerged in the self curing acrylic resin material throughout the procedure. The liquid resin 37 fills the cavity 24 and is forced out into the exhaust tube 28 until it is stopped by the filter 30 provided intermediate the exhaust conduit tube portions 28 and 28'. The inlet tube 27 is then clamped between its protrusion from the cup 36 and its entrance to the patient's mouth. This prevents the acrylic from running back out of the inlet tube 27 when vacuum on the exhaust side of the mold is released.

The vacuum is then released at the pump 32 and the acrylic is allowed to cure in the mold 14. After the acrylic is cured, cuts are made in both the inlet and outlet fittings 25 and 26 at their point of entry into the mold 14. The freed portions of the inlet and outlet assemblies are then set aside leaving the mold 14 filled with the acrylic in the mouth. At this time, the mold 14 is removed from the mouth and set aside. The cured acrylic resin remains in the mouth with two vertical sprues which were formed in the holes 15 and 16. These sprues are cut off the restoration flush with the desired contour of the restoration. The occlusion of the acrylic restoration 38 is then checked and corrected if necessary.

The restoration 38 is then removed from the patient's mouth whereupon it is finished and polished in the usual manner. The polished restoration is then cemented in place in the usual manner and is retained in the patient's mouth until the permanent restoration can be made.

Throughout this specification, the terms "prosthesis" and "restoration" have been used more or less interchangeably to mean any artificial device which replaces or restores missing teeth or missing portions of worn or broken teeth to the original contour of the teeth or to a corrected contour as determined by a dentist. The example of a temporary bridge for capping two broken front teeth is given for purpose of illustration only, of one form of prosthesis which may be made by the method of this invention. The temporary bridge 38 indicated by the stippled area in FIG. 12 is a one piece molded cap for the four front teeth 20–23 illustrated in FIG. 6. The contour of the individual teeth and the crevices between the individual teeth are precisely formed by the method and apparatus of this invention. By evacuating the mold cavity to a high vacuum level and relying on the atmospheric pressure acting on the surface of the liquid resin in the open supply vessel to push the liquid resin into the evacuated mold cavity, the mold cavity is completely filled with the liquid resin. Thus, voids in the prosthesis which would result from air entrapment are avoided.

The use of a hand operated vacuum pump is preferred in this invention because of the ease in obtaining the desired level of vacuum and stopping the operation of the pump when desired. While the possible use of motor operated pump is not excluded, if the requisite controls can be provided, the use of motor operated pump is not preferred because of the simplicity and ease of control of commercially available hand operated vacuum pumps.

While various types of elastomers may be used to form the elastomeric mold 14, one which has been found to be satisfactory is the dental silicone base impression material sold under the trademark Jelcone R by The L. D. Caulk Co., a Division of Dentiply International, Inc.

The prosthesis forming material may also be one of various self curing synthetic resin materials used in dentistry. One such material comprises an acrylic resin forming liquid and powder sold under the trade name Trim by the Harry J. Bosworth Company. The liquid and powder are mixed in the cup 36 to form a thin liquid mixture capable of flowing through the inlet tube 27 into the mold cavity 24 as shown in FIG. 10 of the drawing. The invention is not limited to the use of acrylic type synthetic resins as other self-curing, non-toxic resin materials adapted for use in forming dental restorations may be used. Care must be taken, however, to select a material which on curing does not generate excessive heat which will injure the patient's mouth.

What is claimed is:

1. A method for forming a dental prosthesis in situ in a patient's mouth for the restoration of one or more missing or broken teeth, comprising taking an impression of the patient's mouth and forming a model of the patient's dentition with a hard setting dental model forming material, correcting the model by filling in the areas of the teeth which are to be restored with model correcting material until the corrected areas conform to the desired size and shape of the restored teeth, forming a negative gasket mold of the tooth areas to be restored, by applying a pliable and curable mold forming elastomeric material over the model and overlapping the boundaries of the tooth areas to be restored in all directions by a predetermined distance, curing the negative mold while it is still on the model, drilling a pair of holes through the gasket mold at opposite ends of the mold cavity, applying a tubular fitting in said pair of holes and connecting a flexible exhaust tube having a filter therein to one of said fittings and a flexible inlet tube to the other of said fittings, cutting down the patient's teeth in the areas to be restored to receive the prosthesis leaving the tooth stumps free of undercuts, coating the tooth stump with an antistick mold lubricant, placing the gasket mold assembly in the patient's mouth over the tooth area prepared for restoration with the free ends of the flexible tubes leading outside of the mouth, attaching the free end of the exhaust tube to a vacuum pump, clamping the inlet tube closed intermediate its free end and said gasket mold, operating said vacuum pump to produce a predetermined vacuum in said mold cavity, and testing whether the gasket mold is sealed with respect to the patietn's mouth by observing whether the vacuum will be maintained after a predetermined vacuum has been obtained and the vacuum pumping ceased, releasing the vacuum if the seal is satisfactory, preparing a mix of self curing acrylic liquid resin in a receptacle, inserting the free end of the inlet tube into the mix of self-curing liquid resin while maintaining said inlet tube clamped closed, operating the vacuum pump to obtain a vacuum of substantially 27 inches of mercury or above in said mold cavity, ceasing the operation of the vacuum pump, releasing the clamp from said inlet tube whereupon atmoshperic pressure acting on the liquid resin in said receptacle forces the liquid resin through said inlet tube into said evacuated mold cavity, allowing said liquid acrylic resin to cure into a solid material, and removing said gasket mold, fittings and tubes from the patient's mouth and from said prosthesis.

2. A method for forming a dental prosthesis in situ in a patietn's mouth for the restoration of one or more missing or broken teeth, comprising forming an elastomeric mold of the tooth areas to be restored by applying a pliable and curable mold forming elastomeric material over a positive model of the patient's jaw requiring restoration and overlapping the boundaries of the tooth areas to be restored in all directions by a predetermined distance, curing the elastomeric mold while it is still on the model, drilling a pair of holes through the elastomeric mold at opposite ends of the mold cavity, applying a tubular fitting each of said pair of holes and connecting a flexible exhaust tube having a filter therein to one of said fittings and a flexible inlet tube to the other of said fittings, cutting down the patient's teeth in the areas to be restored to receive the prosthesis leaving the tooth stumps free of undercuts, placing the elastomeric mold with attached fittings and tubes in the patient's mouth over the tooth area prepared for restoration with the free ends of the flexible tubes leading outside of the mouth, attaching the free end of the exhaust tube to a vacuum pump, clamping the inlet tube closed intermediate its free end and said elastomeric mold, operating said vacuum pump to produce a predetermined vacuum in said mold cavity, and testing whether the elastomeric mold is sealed with respect to the patient's mouth by observing whether the vacuum will be maintained after a predetermined vacuum has been obtained and the vacuum pumping ceased, releasing the vacuum if the seal is satisfactory, preparing a mix of self curing liquid resin in a receptacle, inserting the free end of the inlet tube into the mix of self curing liquid resin while maintaining said inlet tube clamped closed, operating the vacuum pump to obtain a predetermined vacuum in said mold cavity, ceasing the operation of the vacuum pump, releasing the clamp from said inlet tube whereupon atmospheric pressure acting on the liquid resin in said receptacle forces the liquid resin through said inlet tube into said evacuated mold cavity, allowing said liquid resin to cure until solid, and removing said elastomeric mold, fittings and tubes from the patient's mouth and from said prosthesis.

3. The method according to claim 2 wherein said mold forming elastomeric material is a silicone base dental impression material.

4. The method according to claim 2 wherein said self curing liquid resin is an acrylic resin.

5. The method according to claim 4 wherein said predetermined vacuum is 27 inches or above of mercury.

6. Apparatus for forming a dental prosthersis in situ comprising an elastomeric mold half which has been prepared over a positive model of the patient's jaw requiring restoration, said mold half having an internal impression of the restoration desired, and boundary flexible gasket areas adapted to seat around the areas bounding the area of a patient's jaw when the mold half is seated over the restoration area in the patient's mouth, a vacuum pump, flexible exhaust conduit means connected between the elastomeric mold half and the vacuum pump, flexible inlet conduit means connected between the elastomeric mold half and an open receptacle for containing a mix of self-curing liquid resin, and means for opening and closing said inlet tube.

7. The apparatus according to claim 6 wherein said exhaust conduit means includes therein a filter for blocking the flow of liquid resin while permitting air to be evacuated from said mold.

8. A method of molding a dental prosthesis in situ in a person's mouth comprising placing a mold having an inner cavity which is an impression of a corrected model of selected teeth over the person's selected teeth which have been prepared for restoration by removing portions thereof, said mold having elastomeric properties and flexible boundary areas which extend beyond the selected teeth, an exhaust port and an inlet port, connecting means for pumping a vacuum inside of said mold to said exhaust port and inlet conduit means for charging a liquid self curing dental prosthesis forming material to said inlet port, preparing said liquid self curing prosthesis forming material in a vessel open to the atmosphere, connecting said inlet conduit means with the liquid prosthesis forming material in said vessel, closing said inlet conduit means, pumping a vacuum inside said mold cavity to a predetermined level whereby atmosphereic pressure outside of said mold forces said boundary areas into sealing contact with underlying portions of the mouth, opening said inlet conduit means whereby atmospheric pressure acting on the liquid prosthesis forming material pushes said liquid prosthesis forming material into the mold cavity, allowing said prothesis forming material to cure and removing said mold from the mouth.

* * * * *